(12) United States Patent
Gupta

(10) Patent No.: US 7,842,723 B2
(45) Date of Patent: Nov. 30, 2010

(54) ASCORBIC ACID—NATURAL SUGAR LACTONE ESTERS FOR COMPREHENSIVE SKIN AND SCALP CARE

(75) Inventor: Shyam K Gupta, Scottsdale, AZ (US)

(73) Assignee: Bioderm Research, Scottsdale, AZ (US)

( * ) Notice: Subject to any disclaimer, the term of this patent is extended or adjusted under 35 U.S.C. 154(b) by 166 days.

(21) Appl. No.: 12/184,340

(22) Filed: Aug. 1, 2008

(65) Prior Publication Data

US 2008/0287533 A1    Nov. 20, 2008

Related U.S. Application Data

(63) Continuation-in-part of application No. 11/163,779, filed on Oct. 31, 2005, now Pat. No. 7,592,002, and a continuation-in-part of application No. 11/309,441, filed on Aug. 6, 2006, now Pat. No. 7,547,454, and a continuation-in-part of application No. 12/139,659, filed on Jun. 16, 2008, and a continuation-in-part of application No. 10/265,000, filed on Oct. 4, 2002, now abandoned.

(51) Int. Cl.
*A01N 43/08* (2006.01)
*A61K 8/73* (2006.01)
(52) U.S. Cl. .................................. 514/474; 424/70.13
(58) Field of Classification Search ........................ None
See application file for complete search history.

(56) References Cited

U.S. PATENT DOCUMENTS 4,845,246 A * 7/1989 Takanohashi et al. ........ 549/315

2003/0017130 A1 * 1/2003 Yu et al. .................. 424/78.03

* cited by examiner

*Primary Examiner*—Michael G Hartley
*Assistant Examiner*—Paul Dickinson

(57) ABSTRACT

This invention relates to esters of ascorbic acid with natural sugar lactones [formula (I)], which are useful for the treatment of skin condition, including age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof;

9 Claims, 4 Drawing Sheets

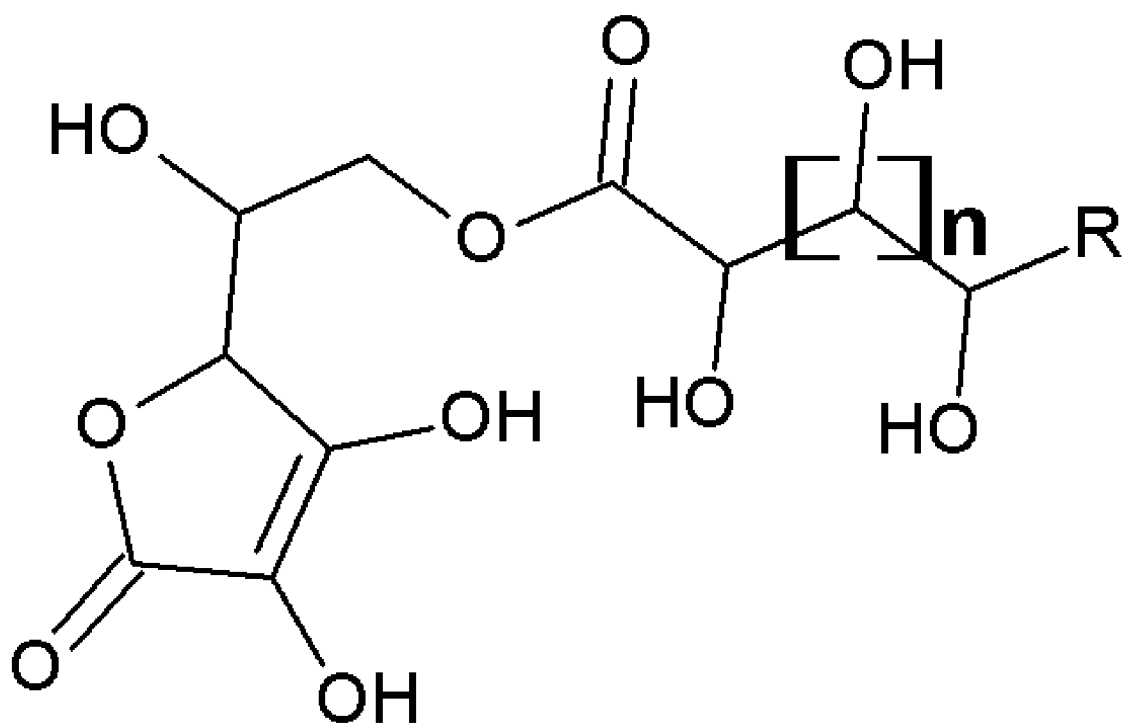
Fig. 1. Ascorbyl Esters

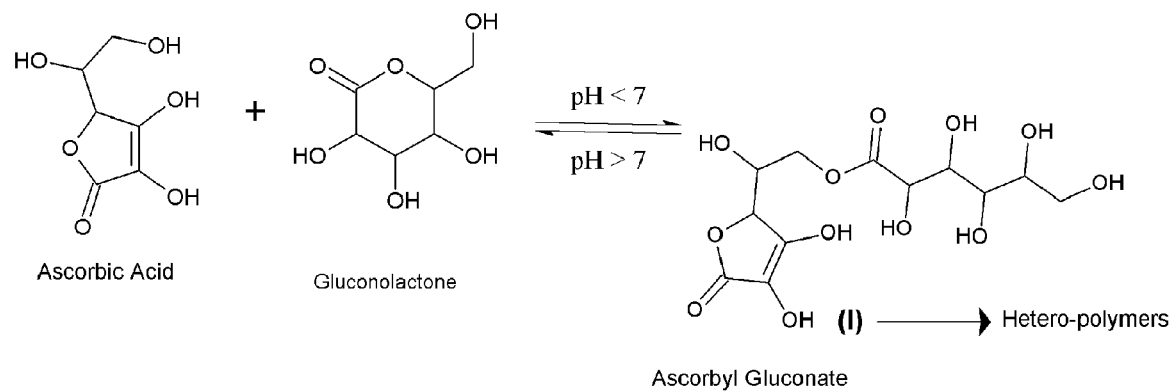
Fig. 2. Process Example of Ascorbyl Esters from Ascorbic Acid
& A Natural Sugar Lactone (Gluconolactone)

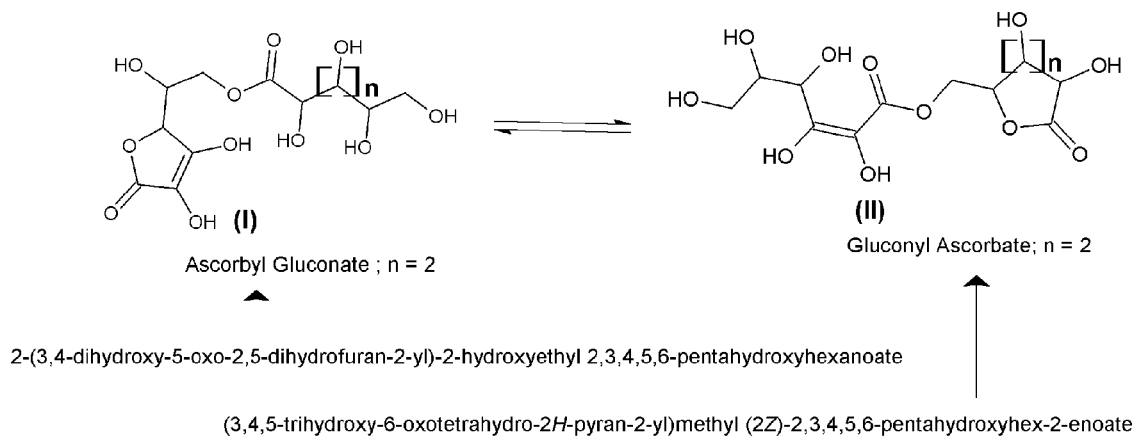
Fig. 3. Isomerism of Ascorbyl Esters

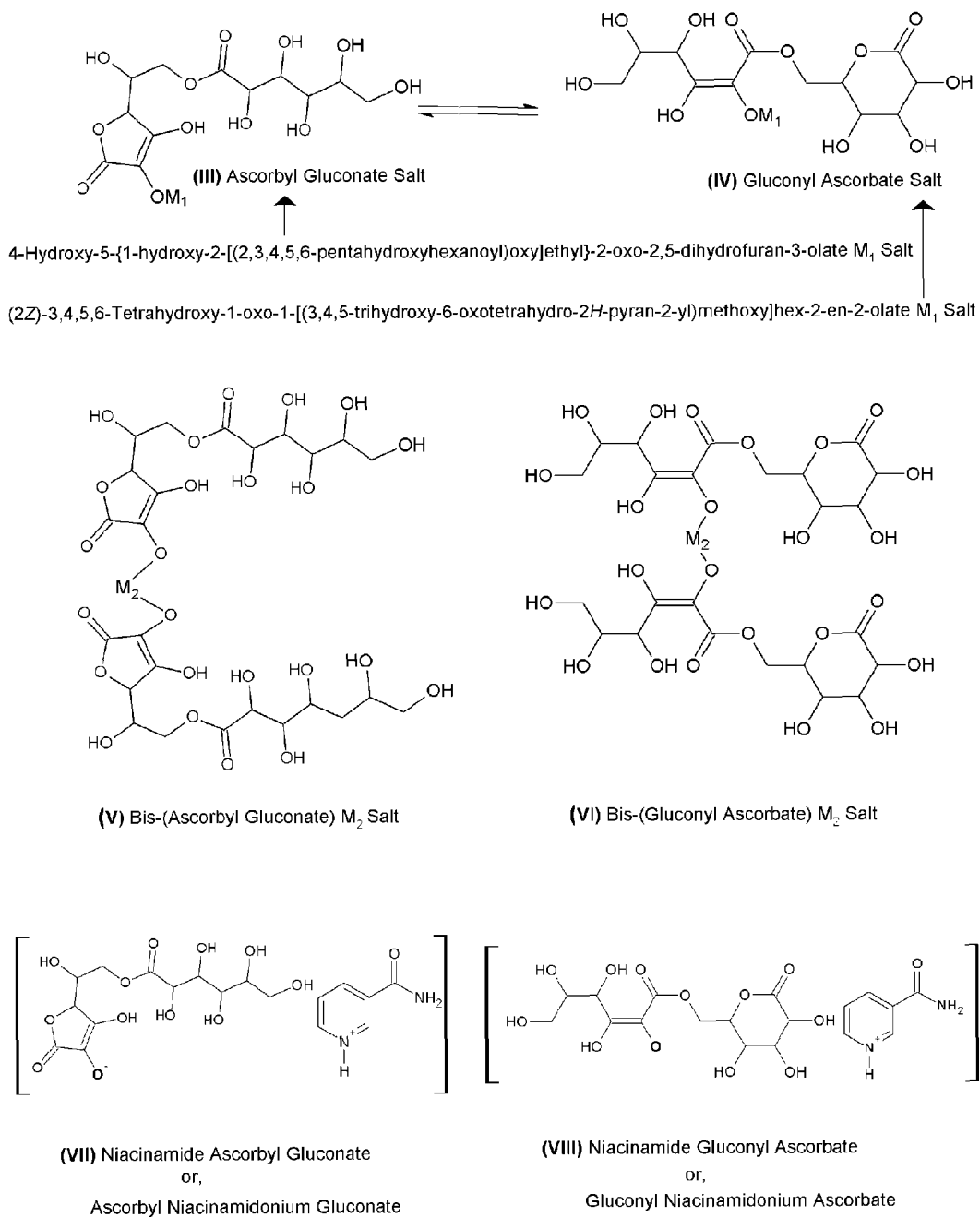
4-Hydroxy-5-{1-hydroxy-2-[(2,3,4,5,6-pentahydroxyhexanoyl)oxy]ethyl}-2-oxo-2,5-dihydrofuran-3-olate M₁ Salt
(2Z)-3,4,5,6-Tetrahydroxy-1-oxo-1-[(3,4,5-trihydroxy-6-oxotetrahydro-2H-pyran-2-yl)methoxy]hex-2-en-2-olate M₁ Salt
Fig. 4. Examples of Salts of Ascorbyl Gluconate Esters

US 7,842,723 B2

ASCORBIC ACID—NATURAL SUGAR LACTONE ESTERS FOR COMPREHENSIVE SKIN AND SCALP CARE

This invention is a continuation-in-part of U.S. patent application Ser. No. 11/163,779 (filed Oct. 31, 2005) that relates to the preparation of conjugates of sucrose and certain internal lactones of polyhydroxy acids, also known as sugar lactones or polyhydroxy lactones, which are useful for cosmetic applications such as dermabrasion, topical exfoliation, age spot removal, wart removal, and hair removal. This invention is also a continuation-in-part of U.S. patent application Ser. No. 11/309,441 (filed Aug. 6, 2006) that relates to certain transition metal complexes of amino acids and hydroxy acids having chemical structure in which one metal atom is concurrently bound to at least one amino acid and at least one hydroxy acid. This invention is also a continuation-in-part of U.S. patent application Ser. No. 12/139,659 (filed Jun. 16, 2008) that relates to certain ketals of ascorbic acid. This invention is also a continuation-in-part of U.S. patent application Ser. No. 10/265,000; filed Oct. 4, 2002 (now abandoned), which discloses stabilized salts of ascorbic acid with certain organic bases.

BACKGROUND OF THE INVENTION

The present invention relates to ascorbyl esters, which are conjugates of ascorbic acid with certain sugar lactones; in their optically active, inactive, or racemic forms (such as d, l, dl, and meso); wherein ascorbyl moiety provides the alcohol part, and the sugar lactone moiety provides the carbonyl part of said ascorbyl esters. These esters are useful for treatment of age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof.

The ascorbyl esters of the present invention are prepared by a novel method, wherein ascorbic acid and isomers, such as isoascorbic acid, which are lactones, and their derivatives with primary hydroxyl group intact, undergo a chemical reaction with certain sugar lactones to form said esters.

This invention also relates to a method of treatment of skin condition including age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof.

DESCRIPTION OF THE RELATED ART

Ascorbic acid and its derivatives have been well studied in the prior art. While ascorbic acid itself has found applications as a vitamin, skin-whitening agent, collagen booster, and an antioxidant, it is also well known for its rapid air oxidation, especially in aqueous solutions. Extensive prior art knowledge exists in the area of stabilized ascorbic acid and its derivatives. For example, Kvitnisky at al. (WO 2004/094369 A2) disclose certain stabilized derivatives of ascorbic acid, and Shibayama (EP 1,666,484) disclose certain stable ascorbic acid phosphate esters.

In a series of disclosures, Yu et al. [U.S. patent applications 20070207222; 20030017130; U.S. Pat. Nos. 6,767,924; 6,384,079; 6,191,167; 6,060,512; 6,051,609; 6,046,238; 5,962,526; 5,942,250; 5,889,054; 5,886,042; 5,886,041; 5,883,128; 5,874,071; 5,856,357; 5,834,510; 5,827,882; 5,807,890; 5,716,992; 5,702,668; 5,691,378; 5,690,967; 5,686,489; 5,684,044; 5,681,853; 5,677,340; 5,677,339; 5,674,903; 5,674,899; 5,670,543; 5,670,542; 5,670,541; 5,668,177; 5,665,576; 5,656,666; 5,656,665; 5,654,340; 5,654,336; 5,652,267; 5,650,440; 5,650,437; 5,650,4336; 5,648,395; 5,648,391; 5,648,388; 5,643,963; 5,643,962; 5,643,961; 5,643,953; 5,643,952; 5,643,949; 5,641,475; 5,637,615; 5,612,376; 5,599,843; 5,589,505; 5,583,156; 5,580,902; 5,578,644; 5,571,841; 5,565,487; 5,561,159; 5,561,155; 5,561,153; 5,556,882; 5,554,651; 5,550,158; 5,550,154; and 5,547,988] have disclosed topical applications of certain hydroxy acids, hydroxy lactones, polyhydroxy acids, and salts and derivatives thereof. The teachings of Yu et al., which are most pertinent to the present invention, can be summarized as follows.

(1). They teach topical skin treating compositions comprising an effective amount of at least one hydroxycarboxylic acid, wherein the at least one hydroxycarboxylic acid is present in the form of a free acid, lactone, or salt.

(2). Where dimeric or polymeric forms of hydroxy acids are claimed, said acids seem to be derived from hydroxy acids.

(3). Dimeric and polymeric forms of hydroxyacids of Yu teachings are reported to be less stable in the presence of water or the like vehicle, as per U.S. patent application 20030017130, paragraph 0244; cosmetic and pharmaceutical formulations comprising the same need to be prepared as anhydrous compositions.

The present invention is significantly different from the above teachings of Yu et al. in the following regards:

(1). The dimeric or polymeric forms of hydroxy acids of the present invention are derived from sugar lactones, at least two of which are used, and both of which should have a different chemical structure, i.e. said dimers are heterodimers, and said polymers are hetero-polymers. For example, ascorbic acid and gluconolactone, both of which are sugar lactones, undergo an unusual chemical reaction, even in the presence of water; to form ascorbyl gluconate, or gluconyl ascorbate, the latter resulting from the isomerization of ascorbyl gluconate, or a mixture thereof; the continuance of this reaction can further lead to the formation of corresponding heteropolymers; in accordance to FIG. 2.

(2). The dimeric or polymeric polyhydroxy acids of the present invention are stable in the presence of water or the like vehicle, hence anhydrous compositions are not required, but can be formulated, if so desired according to consumer or marketing needs.

Additional prior art references related to the present invention are discussed below.

Bharucha et al. (U.S. Pat. No. 4,153,613), Satoh et al. (U.S. Pat. No. 5,194,445), and Terao et al. (U.S. Pat. Nos. 4,780,549 and 4,959,362) disclose acetals and ketals of ascorbic acid with certain aldehydes or ketones.

Vermeer (U.S. Pat. No. 5,624,906) discloses a method for reacting certain hydroxy lactones with amines to form aldonamides. Stockinger (U.S. Pat. No. 6,472,489) discloses similar amine-based polymers.

Narain et al. (Polymer International, vol. 51, No. 1, pp. 85-91, 2002) disclose polymers of gluconolactone with amino methacrylic acid.

Tsutsumi et al. (Macromolecules, vol. 37, No. 16, pp. 5971-5976, 2004) report the preparation of polymeric esters from a sugar lactone, gluconolactone, and a polyhydroxy acid, citric acid.

U.S. Pat. No. 6,559,275 teaches the polymerization of a non-sugar lactone, caprolactone, to form polyesters.

U.S. Pat. No. 6,472,489 teaches the reaction of polyallyl amine with a lactone to form amine-based polymers.

EP 1122275 discloses polymers from gluconolactone.

Klee et al. (U.S. Pat. No. 6,998,111) disclose certain ascorbic acid derivatives.

The topical application of ascorbic acid and its derivatives for the treatment of skin condition has been well practiced in the prior art. The poor stability of ascorbic acid in topical compositions, especially those that contain water, is well known. There have been numerous attempts to provide stable ascorbic acid derivatives. However, most of such derivatives have received poor consumer application due to a combination of several drawbacks, which include their commercial unavailability, high cost, and reduced antioxidant, collagen boosting and skin whitening benefits. Some of such prior art examples are noted below, the detailed perusal of which would serve to illustrate the point made above.

Anderson et al. (U.S. patent application Ser. No. 20060189579) disclose stabilization of ascorbyl phosphate by coating with a lipid.

Buononato et al. (U.S. patent application Ser. No. 20040157800) disclose L-carnitine and lower alkanoyl L-carnitine ascorbyl derivatives and topically applicable cosmetic compositions comprising same as active ingredients.

Kutney et al. (U.S. patent application Ser. No. 20030232797) disclose certain steroidal derivatives of ascorbic acid and use thereof in treating or preventing various conditions, diseases, and disorders.

Perricone et al. (U.S. Pat. No. 6,162,419) disclose certain stabilized ascorbyl compositions.

Streicher et al. (U.S. Pat. No. 6,143,906) disclose certain ascorbyl sorbates.

Hamano et al. (U.S. Pat. No. 5,879,692) disclose tocopheryl ascorbyl phosphate-cyclodextrin clathrates, and topical dermal compositions containing said clathrates.

Ptchelintsev (U.S. Pat. Nos. 5,780,504; 5,607,968) discloses certain topical alkyl-2-O-L-ascorbyl-phosphates.

Kaiser et al. (U.S. Pat. No. 5,420,302) disclose preparation of stable calcium L-ascorbate 2-phosphate.

Pauling et al. (U.S. Pat. No. 5,210,220) disclose certain ascorbyl phosphates as stabilized ascorbic acid derivatives.

McAuliffe et al. (EP 1,833,881) disclose certain ester derivatives of ascorbic acid and 2-keto acids.

Shibayama et al. (EP 1,666,484) disclose certain stable esters of ascorbyl phosphate, which are useful as skin whitening agents.

Gupta (U.S. patent application Ser. No. 20040034094) discloses certain stabilized compositions of ascorbic acid.

Marion (EP 1,637,124) discloses a combination of water-soluble ascorbic acid derivative and a porous polyamide for skin care compositions.

Vromen (EP 1,688,130) discloses certain stable preparations of ascorbic acid that contain micronized ascorbic acid in an anhydrous base.

Mathur (U.S. Pat. No. 4,096,240) discloses niacinamide ascorbate for skin whitening application. Meisner (U.S. patent application Ser. No. 20080125395) discloses a topical preparation of ascorbic acid.

Roomi et al. (U.S. Pat. No. 7,230,124) disclose certain derivatives of ascorbic acid with lysine.

Ruhe (U.S. Pat. No. 6,602,906) discloses ascorbic acid ketal of acetone for topical compositions.

Castiel et al. (U.S. patent application Ser. No. 20020042380) disclose 2,3-substituted ascorbic acid derivatives for skin care.

Zimmermann et al. (U.S. patent application Ser. No. 20080124409, and references cited therein) disclose topical skin compositions, their preparation, and their use that contain ascorbic acid and its derivatives.

BRIEF DESCRIPTION OF THE SEVERAL VIEWS OF THE DRAWINGS

[FIG. 1]. Ascorbyl Esters.

[FIG. 2]. Process Example of Ascorbyl Esters from Ascorbic Acid and A Sugar Lactone (Gluconolactone).

[FIG. 3]. Isomerism of Ascorbyl Esters.

[FIG. 4]. Examples of Salts of Ascorbyl Gluconate Esters

DETAILED DESCRIPTION

The present invention relates to esters of ascorbic acid, including ascorbic acid isomers and their derivatives having their primary hydroxyl group intact, with certain sugar lactones; said lactones as further defined in "The Organic Chemistry of Sugars", Levy and Fugedi, CRC Press (Taylor and Francis Division). These esters in their optically active, inactive, or racemic forms (such as d, l, dl, and meso) [FIG. 1], and polymers thereof, are useful for topical applications that include skin antiaging, wrinkles reduction, age spot reduction, skin whitening, skin brightening, scar tissue reduction, acne reduction, skin exfoliation, reduction of damage from UV and radiation, mild skin exfoliation, dandruff reduction, and stretch marks reduction.

[FIG. 1];

Wherein, n=0, 1, 2, or 3;

R=H, —$CH_2OH$, —CH(OH)—$CH_2OH$, and —CH(OH)—CH(OH)—$CH_2OH$.

This invention also relates to a method of treatment of skin condition, including age spots, acne, loss of cellular antioxidants, collagen loss, loss of skin pliability, loss of skin suppleness, skin wrinkles including fine lines, oxidation, damage from radiation, malfunction of matrix metalloproteases, malfunction of tyrosinases, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof.

The said esters of ascorbic acid with sugar lactone are prepared by a novel method, wherein ascorbic acid, or its certain derivative or salt with a free primary hydroxyl group, undergoes a chemical reaction with said lactone, an example of which is illustrated in FIG. 2.

[FIG. 2].

This is unprecedented, as ascorbic acid, which itself is a sugar lactone, does not react with itself in accordance to FIG. 2 to form the corresponding homo-dimer compound, ascorbyl ascorbate. The chemical reaction of two different sugar lactones to form hetero-dimeric or hetero-polymeric compounds in accordance to FIG. 2 is thus both surprising and unexpected. Moreover, said hetero-dimeric ascorbyl compounds, surprisingly and unexpectedly, can exist in thermodynamic equilibrium with their isomeric structural forms, as illustrated in FIG. 3. To clarify this matter further, a dimer is a chemical or biological entity consisting of two subunits called monomers, which are held together by either intramolecular forces (covalent bonds) or weaker intermolecular forces. Molecular dimers are often formed by the reaction of two identical compounds e.g.: 2A→A-A. The term homodimer is used when the two molecules are identical (e.g. A-A) and heterodimer when they are not (e.g. A-B). A homopolymer is A polymer resulting from the polymerization of a single monomer; a polymer consisting substantially of a single type of repeating unit. A heteropolymer or copolymer is a polymer derived from two (or more) monomeric species, as opposed to a homopolymer where only one monomer is used.

[FIG. 3].

The process of the preparation of the esters of ascorbic acid of the present invention comprises (i) the combining of a sugar lactone and ascorbic acid or its said derivative, and (ii) a solvent or reaction medium agent, and (iii) heating at 50 to 120 C.

The said esters of ascorbic acid of the present invention are made, as mentioned above, by the reaction of ascorbic acid and its isomers and derivatives having a free primary hydroxy group, with a sugar lactone. This reaction is best carried out under acidic pH conditions, preferably from 2.5 to 6.5, and most preferably from 3.0 to 5.5. A solvent medium can be used, which is selected from, but not limited to water, ethanol, ethylene glycol, propylene glycol, butylene glycol, pentylene glycol, hexylene glycol, polyethylene glycol, polypropylene glycol, glycerin, Diglycerin, polyglycerol, sorbitol, polysorbate, methylpropanediol, ethoxydiglycol, dimethyl sulfoxide, N-methylpyrrolidone, pyrrolidone, and combinations thereof. The suitable reaction temperature is from 50 to 120 degrees Celsius (C), preferably from 60 to 100 C, and most preferably from 60 to 80 C. The said sugar lactones include, but not limited to gluconolactone, galactonolactone, glucuronolactone, galacturonolactone, gulonolactone, glucoheptonolactone, ribonolactone, saccharolactone, hydroxycitric acid lactone, pantoyllactone, mannonolactone, Garcinia lactone, arabinolactone, isopropylidene Ribonolactone, Glucooctanolactone, Erythronolactone, isocitric acid lactone, Glyceromannoheptonolactone, and galactoheptonolactone.

The esters of ascorbic acid of the present invention can be selected from ascorbyl gluconate, ascorbyl galactonoate, ascorbyl glucuronoate, ascorbyl saccharate, ascorbyl pantoyloate, ascorbyl mannonoate, ascorbyl garcinoate, ascorbyl hydroxycitrate, ascorbyl arabinoate, ascorbyl isopropylidene ribonoate, ascorbyl glucooctanoate, ascorbyl erythronoate, ascorbyl isocitrate, ascorbyl glyceromannoheptonoate, ascorbyl galactoheptonoate, isoascorbyl gluconate, isoascorbyl galactonoate, isoascorbyl glucuronoate, isoascorbyl saccharate, isoascorbyl pantoyloate, isoascorbyl mannonoate, isoascorbyl garcinoate, isoascorbyl hydroxycitrate, isoascorbyl arabinoate, isoascorbyl isopropylidene ribonoate, isoascorbyl glucooctanoate, isoascorbyl erythronoate, isoascorbyl isocitrate, isoascorbyl glyceromannoheptonoate, isoascorbyl galactoheptonoate, and combinations thereof.

The corresponding isomers of the above esters of ascorbic acid, formed via thermodynamic equilibrium according to FIG. 3, includes gluconyl ascorbate, galactonyl ascorbate, glucuronyl ascorbate, saccharyl ascorbate, pantoylyl ascorbate, mannonyl ascorbate, garcinyl ascorbate, hydroxycitryl ascorbate, arabinyl ascorbate, isopropylidene ribonyl ascorbate, glucooctanyl ascorbate, erythronyl ascorbate, isocitryl ascorbate, glyceromannoheptonyl ascorbate, galactoheptonyl ascorbate, gluconyl isoascorbate, galactonyl isoascorbate, glucuronyl isoascorbate, saccharyl isoascorbate, pantoylyl isoascorbate, mannonyl isoascorbate, garcinyl isoascorbate, hydroxycitryl isoascorbate, arabinyl isoascorbate, isopropylidene ribonyl isoascorbate, glucooctanyl isoascorbate, erythronyl isoascorbate, isocitryl isoascorbate, glyceromannoheptonyl isoascorbate, galactoheptonyl isoascorbate, and combinations thereof.

This reaction is both surprising and unexpected, as ascorbic acid and arabinolactone, for example, both of which have a five-membered lactone ring but it is arabinolactone ring that appears to open first to react with the primary hydroxyl group of ascorbic acid. For some reason, the five-membered lactone ring of ascorbic acid with an internal double bond seems to be more stable than the five-membered ring of ribonolactone that does not have an internal double bond. Similarly, five-membered lactone ring of ascorbic acid seems to be more stable over a six-membered lactone ring, for example, that of gluconolactone, in which case gluconolactone ring seems to open first to react with the primary hydroxyl group of ascorbic acid.

Also, this process can be performed in a single step via a novel in-situ method. In the preparation of a skin lotion or cream composition, for example, all other ingredients of said composition can be mixed and processed and said sugar lactone and ascorbic acid or its said derivative with a free primary hydroxyl group can then be added to the composition, wherein the corresponding ascorbyl ester is formed in-situ. Alternatively, sugar lactone can first be reacted with ascorbic acid or its said derivative in the presence of a solvent as a processing aid, and resulting ascorbyl ester can then be utilized in any subsequent composition.

Certain divalent and polyvalent metal ions can also be present in the compositions of the present invention. The examples of such metal ions include lithium, sodium, potassium, calcium, magnesium, barium, zinc, copper, manganese, vanadium, chromium, cobalt, and iron. Certain amines, nitrogen heterocyclic and nitrogen heteroaromatic, ammonium, and nitrogen amphoteric compounds can also be present in the compositions of the present invention. The said metal, amine, ammonium, nitrogen heterocyclic, nitrogen heteroaromatic, and amphoteric compounds can be in the form of a salt derivative of ascorbyl esters of the present invention. The examples of metal ions include, but not limited to lithium, sodium, potassium, calcium, magnesium, barium, zinc, copper, manganese, vanadium, chromium, cobalt, and iron. The examples of said amine, nitrogen heterocyclic and nitrogen heteroaromatic, and ammonium compounds includes ammonia, triethanolamine, various cyclic and alicyclic mono alkyl, di-alkyl, and tri-alkyl amines, glucosamine, glutathione, allantoin, creatine, creatinine, chondroitin, chitosan, carnosine, niacinamide, amino acids, inorganic and organic salts of amino acids, peptides, and like. The examples of the salt-forming agents for certain ascorbic acid salts disclosed earlier (U.S. patent application Ser. No. 10/265,000; filed Oct. 4, 2002; now abandoned) are also applicable in the present invention.

The salts of ascorbyl esters of the present invention comprises an inorganic salt of said ester; an organic base or an acid salt of an organic base; or an amphoteric compound or an inorganic salt of an amphoteric compound; that can chemically bind with said ascorbyl ester molecule to form in-situ an ascorbyl ester salt of the corresponding base. The formulation is particularly suited for, but not limited to, use in cosmetic and medical fields as a composition to be applied externally to the skin and hair of an individual. Additional skin beneficial and cosmetically desirable ingredients can be added to the formulation.

As is known in the art, the union of an acid and base leads to the formation of a salt as part of a neutralization reaction. In the case of diacid and triacid bases, and of dibasic and tribasic acids, the mutual neutralization may vary in degree, producing respectively basic, neutral, or acid salts. A method for synthesizing single component, or multi-component salts of ascorbyl esters of the present invention has now been discovered, which includes reacting said ester in water with at least one organic base to form a single component salt, or several organic bases to form a multi-component salt, the quantity of organic base or bases depending upon the molecular weight and acidity of organic base or bases to form salts with ascorbic acid. While the preparation of such salts is not difficult, as set forth in U.S. Patent Application No. 20020058704 to Malik et al., the preparation of such salts of ascorbyl esters, in water solution, that are stable in the presence of water and air, has not been disclosed in the prior art.

To illustrate the scope of this invention, the equation 1 shows the formation of an ascorbyl ester salt of an organic base in water solution;

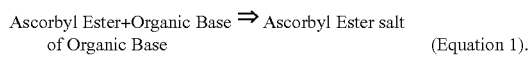

Ascorbyl Ester+Organic Base ⇒ Ascorbyl Ester salt of Organic Base    (Equation 1).

Thus, by mixing said ascorbyl ester, for example ascorbyl gluconate, with glucosamine in equimolar amounts in water solution, one mole of Glucosamine ascorbyl gluconate is produced in-situ, as illustrated in Equation 2.

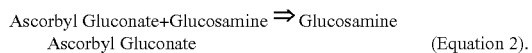

Ascorbyl Gluconate+Glucosamine ⇒ Glucosamine Ascorbyl Gluconate    (Equation 2).

Additionally, by mixing a metal salt of said ascorbyl ester with an acid salt of an organic base, ascorbyl ester salt of an organic base can be prepared in-situ, as exemplified in Equation 3.

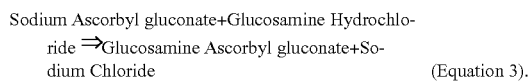

Sodium Ascorbyl gluconate+Glucosamine Hydrochloride ⇒Glucosamine Ascorbyl gluconate+Sodium Chloride    (Equation 3).

Multi-component ascorbyl ester salt compositions can thus be made in-situ by mixing the reacting components in proportionate molar quantities in water solution, as exemplified in Equation 4.

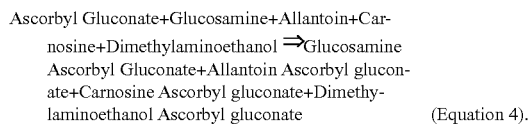

Ascorbyl Gluconate+Glucosamine+Allantoin+Carnosine+Dimethylaminoethanol ⇒Glucosamine Ascorbyl Gluconate+Allantoin Ascorbyl gluconate+Carnosine Ascorbyl gluconate+Dimethylaminoethanol Ascorbyl gluconate    (Equation 4).

The chemical structure of some of said salts of ascorbyl esters is illustrated in FIG. 4.

[FIG. 4];
Wherein,
$M_1$=Monovalent metals or cations=Li, Na, and K (formula III and IV); ammonium, alkyl ammonium, and nitrogen heterocyclic base; and
$M_2$=Divalent metals=Ca, Mg, Zn, Mn, Cu, Ba, V, Mo, Co, and Fe (formula V and VI).

The chemical structure of a salt of ascorbyl gluconate with a nitrogen heterocyclic base, for example niacinamide, is illustrated in FIG. 4 (formula VII and VIII).

It is well known that the mixtures of several ascorbyl salts are more beneficial than the use of single components alone, for example, U.S. Pat. No. 6,110,966 describes a triple action complex containing three forms of ascorbic acid, which provides the triple action of a major anti-oxidant, an anti-inflammatory and a collagen booster. The triple action complex contains ascorbic acid, sodium ascorbate, and ascorbyl glucosamine as the three forms of vitamin C (ascorbic acid). U.S. Pat. No. 5,626,883 describes a vitamin C supplement comprising ascorbic acid, ascorbyl palmitate, niacinamide ascorbate, calcium ascorbate, magnesium ascorbate, potassium ascorbate, and sodium ascorbate which together can be administered to a human to avoid the transitory initial suppression of human NK cell activity which is present when ascorbic acid alone is administered. U.S. Pat. No. 5,895,652 describes an ascorbate-citrus antioxidant complex, including: Vitamin C (from calcium, magnesium and niacinamide ascorbate), Vitamin C, ascorbyl palmitate (preferably fat soluble), and acerola juice powder (a natural form of Vitamin C) mixture for enhanced benefits. In these examples, various forms of ascorbic acid are individually prepared, and then mixed in correct proportions. The mixtures of ascorbyl esters and salts of ascorbyl esters can be prepared with much ease for the composition of cosmetic or pharmaceutical products for topical application that can provide improved efficacy and better chemical stability.

The present invention also discloses a method of topical application of said Ascorbyl esters, their isomers, and salts thereof, for the treatment of skin condition, comprising; (i) the topical application of said esters at a desired site in a sufficient quantity; and, wherein, (ii) said application having been done either by a manual or a mechanical method, or a combination thereof; and, wherein (iii) said application is repeated as necessary, and, wherein (iv) said application causes the desired treatment of said skin condition. A carrier, or base, or composition can also be used in combination with ascorbyl esters for the said method of treatment.

Skin Brightening and Antiwrinkle-Antiaging Applications.

The Ascorbyl esters, their isomers, and salts thereof of the present invention provide an unexpected reduction of melanin, especially when administered via method of the present invention. The mechanism of this action is not clear at this stage. However, it is speculated that the ascorbyl esters of the present invention dissociate into their original constituents (ascorbic acid and sugar lactone, for example) after their penetration into skin and having reached the physiological pH of about 7.4; therein, the ascorbate portion of the Ascorbyl esters reduces melanin color by chemical reduction of color forming conjugated double bonds of melanin. Additionally, sugar lactone part of the Ascorbyl esters assists the removal of cells containing melanin. This unprecedented dual mechanism results in a superior brightening of dark skin, reduction of age spots, and prevention of skin darkening upon exposure to sun and UV. Although the precise mechanism is unknown, the beneficial affect of said esters in the treatment of skin condition is further established by the results of two human clinical testing disclosed herein.

Collagen Synthesis Enhancement.

The Ascorbyl esters, their isomers, and salts thereof, of the present invention provide a surprising and unexpected enhancement of collagen in skin. This results in increased suppleness and pliability of skin and wrinkles reduction. This is further established by the results of two human clinical testing disclosed herein.

Antioxidant Application.

The Ascorbyl esters, their isomers, and salts thereof, of the present invention provide surprisingly unexpected intracellular and extracellular antioxidant properties. It is usually either an extracellular or an intracellular antioxidant benefit that is provided by any single agent. Thus, the Ascorbyl esters of the present invention offer novel multi-function benefits. This is of great commercial and consumer significance with current trend of worldwide aging population.

With an aging population, there has been an increase in the study of aging as it relates to the human body and, more particularly, human skin. For example, the treatment of aging skin exhibited by the presence of fine lines, wrinkles, and the like has received a great deal of attention. The dermal signs of aging such as fine lines, wrinkles, laxity, and hyperpigmentation have been fought through many tactics including surgery, laser treatment and cosmetics. Cosmetic treatments include the use of various creams and lotions to alter the effects of dermal aging. Much of the literature in the prior art focuses on the use of a single primary component to prevent one of several deleterious aging affects. For example, one tactic has been to use one or more hydroxy acids or retinoic acid to stimulate the re-growth of dermal cells, without other components. This approach is flawed because it does not recognize that aging is caused by the deleterious interaction of multiple agents on the skin, from multiple sources, causing damage to the skin through multiple simultaneous damage pathways.

More comprehensive studies have found that environmental factors, such as stress, sun exposure, and impurities in food, water, and air, also adversely effect components of the epidermal and dermal layers of the skin which, in turn, impact and alter the appearance of the skin and lead to an appearance of premature aging. For example, factors such as free radicals, reactive nitrogen species ("RNS"), reactive oxygen species ("ROS"), and other oxidizing species ("OOS") that may or may not possess characteristics of each free radicals, RNS, and ROS, can adversely impact the human body including the skin. Particular factors within the groups noted above that have been found to impact and adversely affect the appearance of the skin include nitric oxide, superoxide radicals, hydrogen peroxide, and hydroxide free radicals. These factors have been variously implicated in a number of skin conditions including photo damage, general aging of the skin, contact dermatitis, wrinkling, lipid peroxidation, enzyme degradation, reduction and breakdown of collagen and/or elastin, degradation and inhibited reproduction of DNA, inflammation, and general damage to the skin tissue.

The ROS species include superoxide (O2-), hydrogen peroxide (H2O2), peroxy radicals (HO2 and RO2) alkyl peroxide (R2O2), hydroxyl radical (OH), alkoxy radical (OR), and singlet oxygen. The OOS species include hypohalous acids (HOX) (where X is chloride, bromide, iodide), Z-amines (where Z is either chlorinated or ammoniated amine containing compounds, the reactive nitrogen species ("RNS") nitric oxide (NO), ammonia, cyclooxygenase, phospholipase A2, phospholipase C and transition metals.

Each of the ROS directly or acting as an intermediate are thought to act on cell membrane and/or other cellular components including organelles and their contents to adversely impact the skin. Thus, there is a need for a topical skin treatment composition and method that provides a defense against each of the ROS, RNS, and OOS noted above. In addition, it would be desirable if such a composition repaired damage caused by the ROS, RNS, and OOS noted above.

The agents and compositions of the present invention are directed to components that provide a defense against the various pathway mechanisms of free radicals, reactive oxygen species, reactive nitrogen species, and other oxidizing species noted above that adversely affect the human body, including the skin. The present inventions, therefore, also include methods for applying the compositions of the invention to the skin, to inhibit the causative factors that adversely affect the skin, and thereby treat and improve the quality of the skin. Generally, the compositions and methods of this invention are directed to the prevention of the adverse or detrimental effects of free radicals, reactive oxygen species, reactive nitrogen species, and other oxidizing species noted above, on the human body, including the skin. Thus, the present invention includes various compositions that include at least one anti-free radical component and/or an anti-superoxide component and/or an anti-hydrogen peroxide component and/or an anti-hydroxyl radical component and/or a chain-breaking component. Moreover, most, if not all, of the above beneficial functions can be provided by multi-functional Ascorbyl esters of the present invention. This is further established by the results of two human clinical testing disclosed herein.

Formulation of Ascorbyl Esters in Topical Compositions.

The Ascorbyl esters, their isomers, and salts thereof, of the present invention can be formulated in various cosmetic and pharmaceutical consumer product compositions, delivery systems, and carrier bases utilizing a variety of delivery systems and carrier bases. Such consumer products include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, band-aids, and balms.

In another preferred aspect, the delivery system or a carrier base are selected in the form of a lotion, cream, gel, spray, thin liquid, body splash, powder, compressed powder, tooth paste, tooth powder, mouth spray, paste dentifrice, clear gel dentifrice, mask, serum, solid cosmetic stick, lip balm, shampoo, liquid soap, bar soap, bath oil, paste, salve, collodion, impregnated patch, impregnated strip, skin surface implant, impregnated or coated diaper, and similar delivery or packaging form.

In another preferred aspect, the delivery system can be traditional water and oil emulsions, suspensions, colloids, microemulsions, clear solutions, suspensions of nanoparticles, emulsions of nanoparticles, or anhydrous compositions. Additional cosmetically or pharmaceutically beneficial ingredients can also be included in the compositions consisting the Ascorbyl esters of the present invention, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, *luffa* particles, polyethylene balls, mica, pH adjusters, processing aids, and combinations thereof.

In another preferred aspect, the compositions further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylans, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomainans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The compositions may include surface-active agents. Surface-active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in The composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecylbenzene sulfonate.

Amphoteric surface-active agents which may be used in The composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL, as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in The composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The compositions comprising the Ascorbyl esters of the present invention may include long chain fatty amines from about C10 to C22 and their derivatives. Specific examples include dipalmitylamine, lauramidopropyldimethylamine, and stearamidopropyl dimethylamine. The compositions of this invention may also include fatty alcohols (typically monohydric alcohols), ethoxylated fatty alcohols, and ditallow phospholipids, which can be used to stabilize emulsion or dispersion forms of the compositions. They also provide a viscosity. Selection of the fatty alcohol is not critical, although those alcohols characterized as having fatty chains of C10 to C32, preferably C14 to C22, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in The compositions comprising the Ascorbyl esters of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in The compositions comprising the Ascorbyl esters of the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the like; amidobetaines and amidosulfobetaines, wherein the $RCONH(CH_2)_3$ radical is attached to the nitrogen atom of the betaine are also useful in this invention.

The anionic, cationic, nonionic, amphoteric or zwitterionic surface-active agents used in The compositions of this invention are typically used in an amount from about 0.1 to 50 percent by weight, preferably from about 0.5 to about 40 percent by weight, more preferably from about 1 to about 20 percent by weight.

The compositions comprising the Ascorbyl esters of the present invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The compositions comprising the Ascorbyl esters of the present invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefines, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The composition comprising the Ascorbyl esters of the present invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20,2-ethylhexyl isononoate, 2-ethylhexyl stearate, C12 to C16 fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions comprising the Ascorbyl esters of the present invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The compositions comprising the Ascorbyl esters of the present invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane-200 fluid having a viscosity of about 1 centistoke. When used, the silicone oils are preferably included in the formulations of this invention at a concentration of 0.1 to 30 weight percent, more preferably 1 to 20 weight percent.

The compositions comprising the Ascorbyl esters of the present invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The compositions comprising the Ascorbyl esters of the present invention may include volatile hydrocarbon oils. The volatile hydrocarbon comprises from about C6 to C22 atoms. A preferred volatile hydrocarbon is an aliphatic hydrocarbon having a chain length from about $C_6$ to $C_{16}$ carbon atoms. An example of such compound includes isohexadecane, under the trade name Permethyl 101A, available from Presperse, South Plainfield, N.J., USA. Another example of a preferred volatile hydrocarbon is C12 to C14 isoparaffin, under the trade name Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The compositions comprising the Ascorbyl esters of the present invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. General examples include quaternary derivatives of cellulose ethers, quaternary derivatives of guar, and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the composition of this invention at a concentration of from 0.1 to 10 weight percent, preferably from 0.2 to 6 weight percent and most preferably from 0.2 to 5 weight percent.

The compositions comprising the Ascorbyl esters of the present invention may include one or more rheological modifiers. The rheological modifiers that can be used in this invention include high molecular weight crosslinked homopolymers of acrylic acid, and Acrylates/C10-30 Alkyl Acrylate Crosspolymer, such as the Carbopol and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropyltrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in The composition of this invention at a concentration of from 0.01 to 12 weight percent, preferably from 0.05 to 10 weight percent and most preferably from 0.1 to 6 weight percent.

The compositions may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The anti oxidants will be present at from 0.01 to 20 weight percent, preferably 0.5 to 10 weight percent and most preferably from 1.0 to 5.0 weight percent of the composition.

The composition comprising the Ascorbyl esters of the present invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis(hydroxypropyl)aminobenzoate, 2-ethylhexyl 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in The composition of this invention will vary depending on the specific UV absorption wavelength(s) of the specific sunscreen active(s) used and can be from 0.1 to 10 percent by weight, from 2 to 8 percent by weight.

The compositions comprising the Ascorbyl esters of the present invention may include one or more preservatives. Example of preservatives, which may be used include, but are not limited to 1,2-dibromo-2,4-dicyano butane (Methyldibromo Glutaronitrile), benzyl alcohol, imidazolidinyl urea, 1,3-bis(hydroxymethyl)-5,5-dimethyl-2,3-imidazolidinedione (e.g., DMDM Hydantoin), methylchloroisothiazolinone and methylisothiazolinone (e.g. Kathon CG), methyl paraben, propyl paraben, phenoxyethanol, ethylhexylglycerin, chlorphenesin, and sodium benzoate, and mixtures thereof.

The compositions comprising the Ascorbyl esters of the present invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the composition of this invention. The treated pigments are then more effective as sunscreen actives and for use in color cosmetics such as make up and mascara.

The compositions comprising the Ascorbyl esters of the present invention can be presented in various forms. Examples of such forms include, but are not limited a solution, liquid, cream, emulsion, dispersion, gel, and thickening lotion.

The compositions comprising the Ascorbyl esters of the present invention may contain water and also any solvent. Examples of acceptable solvents include, but are not limited to monohydric alcohols, such as alkanols having 1 to 8 carbon atoms (like ethanol, isopropanol, benzyl alcohol and phenylethyl alcohol), polyalcohols, such as alkylene glycols (like glycerin, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture from 0.1 to 70 percent by weight, relative to the weight of the total composition.

The composition comprising the Ascorbyl esters of the present invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The compositions comprising the Ascorbyl esters of the present invention can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions comprising the Ascorbyl esters of the present invention for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions comprising the Ascorbyl esters of the present invention may be prepared as oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, humectants, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions comprising the Ascorbyl esters of the present invention for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions comprising the Ascorbyl esters of the present invention are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVP (polyvinyl pyrrolidone), PVP/dimethylaminoethylmethacrylate copolymer, PVP/eicosene copolymer, PVP/ethyl methacrylate/methacrylic acid copolymer, PVP/hexadecene copolymer, PVP/VA (vinyl acetate) copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Hair care," Cosmetics and Toiletries, 103 (1988), incorporated herein by reference. Other synthetic polymers that may be used with the present invention can be referenced in the CTFA Dictionary, Fifth Edition, 2000, incorporated herein by reference.

The cosmetic compositions comprising the Ascorbyl esters of the present invention may be formulated in a wide variety of form, for non-limited example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. In detail, the cosmetic composition of the present invention can be provided in a form of skin softener (skin lotion), astringent lotion, nutrient emulsion (milk lotion), nutrient cream, message cream, essence, eye cream, cleansing cream, cleansing foam, cleansing water, facial pack, spray or powder.

The carrier comprising the Ascorbyl esters of the present invention may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonite, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solution and emulsion comprising the Ascorbyl esters of the present invention may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension comprising the Ascorbyl esters of the present invention may comprise liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, agar and tragacanth or mixtures of these ingredients.

The formulation of cleansing compositions comprising the Ascorbyl esters of the present invention with surfactant may comprise aliphatic alcohol sulfate, aliphatic alcohol ether sulfate, sulfosucinnate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester or mixtures of these ingredients.

Additional antioxidant ingredients and compositions comprising the Ascorbyl esters of the present invention can be included, and selected from but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), α-Lipoic acid, Niacinamide lipoate, Glutathione, Andrographolide (*Andrographis paniculata*), Carnosine, Niacinamide, *Potentilla erecta* extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof.

The blood micro-circulation improvement ingredients and compositions can be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), *Emblica* extract (*Phyllanthus emblica* extract), Asiaticoside (*Centella asiatica* extract), *Boswellia* Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis Vinifera*) leaves, apigenin, phytosan, luteolin, and combinations thereof.

The anti-inflammatory ingredients or compositions can be selected from, but not limited to, at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, and *Emblica* extract. Anti-inflammatory composition can additionally be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), *Emblica* extract (*Phyllanthus emblica* extract), Asiaticoside (*Centella asiatica* extract), *Boswellia* Extract (*Boswellia serrata*), Sericoside, Visnadine, Thiocolchicoside, Grapeseed Extract, Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis-Vinifera*) leaves, apigenin, phytosan, luteolin, and combinations thereof.

EXAMPLES

All quantities are in weight percent amounts. The examples do not limit the scope of the present invention.

Example 1

Process for the Preparation of Ascorbyl Gluconate

Ingredients. (1) Water 5.0 (2) Ascorbic Acid 5.0 (3) Gluconolactone 5.0 (4) Butylene Glycol 85.0. Procedure. Ingredients 1 to 4 are mixed and heated at 60 to 65 C till a solution is obtained, then cooled to room temperature. A solution of ascorbyl gluconate in butylene glycol—water is thus obtained, which is used subsequently for other preparations.

Example 2

Comprehensive Skin & Hair Care Serum Containing in-Situ Generated Ascorbyl Gluconate Ingredients. (1) Water 5.0 (2) Ascorbic Acid 5.0 (3) Gluconolactone 10.0 (4) Butylene Glycol 52.0 (5) Diglycerol 20.0 (6) Dow Corning Cosmetic Wax 2501 4.0 (7) Structure Plus 4.0. Procedure. Ingredients 1 to 5 are mixed and heated at 60 to 65 C till a solution is obtained then cooled to 35 to 40 C and ingredient 6 and 7 are added with mixing to a desired viscosity. It is cooled to room temperature. A serum-like product is obtained, pH 3.1. It is marked Serum A in the clinical testing described herein.

A control sample without any gluconolactone, and with proportionately increased amount of butylene glycol, was also prepared (pH 3.5) and labeled Serum B in the clinical testing described herein.

Example 3

Process for the Preparation of Zinc Ascorbyl Gluconate

Ingredients. (1) Water 5.0 (2) Sodium Ascorbate 5.0 (3) Gluconolactone 5.0 (4) Butylene Glycol 85.0. Procedure. Ingredients 1 to 4 are mixed and heated at 60 to 65 C till a solution is obtained, then cooled to room temperature. A solution of zinc ascorbyl gluconate in butylene glycol—water is thus obtained, which is used subsequently for other preparations.

Example 4

Process for the Preparation of Sodium Ascorbyl Gluconate

Ingredients. (1) Water 5.0 (2) Sodium Ascorbate 5.0 (3) Gluconolactone 5.0 (4) Butylene Glycol 85.0. Procedure. Ingredients 1 to 4 are mixed and heated at 60 to 65 C till a solution is obtained, then cooled to room temperature. A solution of sodium ascorbyl gluconate in butylene glycol—water is thus obtained, which is used subsequently for other preparations.

Example 5

Skin Discoloration and Age Spots Serum Containing in-Situ Generated Ascorbyl Gluconate Ingredients. (1) Water 5.0 (2) Ascorbic Acid 5.0 (3) Resacetophenone 2.0 (4) Butylene Glycol 55.0 (5) Diglycerol 20.0 (6) Dow Corning Cosmetic Wax 2501 4.0 (7) Glucono-delta-lactone 5.0 (8) Structure Plus 4.0. Procedure. Ingredients 1 and 2 are mixed and heated at 60 to 65 C till a solution is obtained. Ingredients 3 to 7 are mixed and heated at 60 to 65 C till a solution is obtained. The two solutions are mixed and heated at 60 to 65 C for 30 to 45 minutes, then cooled to 35 to 40 C and ingredient 8 is added with mixing to a desired viscosity. It is cooled to room temperature. A serum-like product is obtained.

Example 6

Skin Whitening Cream

Ingredients. (1) Water 55.0 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia* Serrata 0.5 (10) Cetyl Dimethicone 1.5 (11) Tetrahydrocurcuminoids 0.5 (12) Shea butter 2.0 (13) Ximenia oil 1.0 (14) Triethyl citrate 5.0 (15) Ascorbyl gluconate 6.0 (16) Paeonol 1.5 (17) Carnosine 0.1 (18) Cyclomethicone, Dimethicone Crosspolymer 2.0 (19) Polysorbate-20 2.0 (20) Ethyl Lactate 12.0. Procedure. Mix (1) to (13) and heat at 70 to 80 C till homogenous. Cool to 40 to 50 C. Premix (14) to (20) and add to batch with mixing. Cool to room temperature. An off-white cream is obtained.

Example 7

Skin Brightening Eye Serum

Ingredients. (1) Butylene Glycol 23.8 (2) Methylpropanediol 25.8 (3) Hydroxypropyl Cellulose 0.25 (4) Mango butter 2.0 (5) Gluconolactone (5.0) (6) Ascorbic acid 10.0 (7) Matrine 1.5 (8) Methylpropanediol 30.35 (9) Preservative 0.8. (10) Titanium Dioxide 0.5. Procedure. Mix (1) to (3) and heat at 85 to 95 C till a clear solution is obtained. Premix all other ingredients and heat to 45 to 50 C. Add premix to main batch and mix, and then cool to room temperature. A white, lotion-like serum is obtained.

Example 8

Anhydrous Eye Cream Serum with Additional Ingredients in a Base

Ingredients. (1) Butylene Glycol 23.0 (2) Methylpropanediol 20.6 (3) Polyamide-3 5.0 (4) Shea butter 0.5 (5) Murumuru butter 0.5 (6) Ximenia oil 0.5 (7) Coleus oil 0.5 (8) Phenoxyethanol 1.0 (9) Methylpropanediol 25.0 (10) Gluconolactone 10.0 (11) Ascorbic acid 10.0 (12) Ellagic acid 1.5 (13) Titanium Dioxide 1.0 (14) Magnolia Bark Extract 0.2 (15) Matrine 0.2 (16) Ethylhexylglycerin 0.3 (17) Fragrance 0.2. Procedure. Mix (1) to (3) at 80 to 90 C till a clear solution is obtained. Add (4) to (7) with mixing, and cool to 50 to 60 C. Make a premix by mixing (8) to (16) at 50 to 60 C with homogenization to a cream consistency. Add premix to main batch with mixing, then cool to 30 to 40 C and add (17) with mixing. Cool to room temperature.

Example 9

A Method of Treatment of Skin Condition with a Carrier or Base

The method of treatment for skin condition comprises;
i) The ascorbyl ester, according to example 1, is mixed with a suitable carrier or base, and
ii) It is applied on an afflicted area in a sufficient quantity, and,
iii) The application is repeated to complete the treatment as desired.

Example 10

A Method of Treatment of Skin Condition with a Delivery System

The method of treatment for skin condition comprises of the following steps;
iv) The ascorbyl ester, according to example 1, is mixed with a suitable delivery system, and
v) It is applied on an afflicted area in a sufficient quantity, and,
vi) The application is repeated to complete the treatment as desired.

Example 11

A Method of Treatment of Skin Condition with Ascorbyl Esters Comprising i. The topical application of said ascorbyl esters at a desired site in a sufficient quantity; and, wherein,
ii. Said application having been done either by a manual or a mechanical method, or a combination thereof; and, wherein
iii. Said application is repeated to complete the treatment as desired, and, wherein
iv. Said topical application causes the desired treatment of said skin condition.

Example 12

Preparation of a Salt of Ascorbyl Ester with Niacinamide

Ingredients. (1) Water 5.0 (2) Ascorbic Acid 5.0 (3) Gluconolactone 5.0 (4) Butylene Glycol 82.5.0 (5) Niacinamide 2.5. Procedure. Ingredients 1 to 4 are mixed and heated at 60 to 65 C till a solution is obtained, ingredient 5 is then added with mixing, and the reaction mixture cooled to room temperature. A solution of niacinamide ascorbyl gluconate in butylene glycol—water is thus obtained.

Stability Testing of Serum A and Serum B.

Example 13

Stability Testing of Serum A

Procedure. The liquid of Example 2, Serum A is stored at room temperature in a container. A lid is laid across the top of the container to slow evaporation. The lid does not prevent ambient air from slowly entering the container. After six months the liquid is still clear and colorless.

Example 14

Stability Testing of Serum B

Procedure. The liquid of Example 2, Serum B is stored at room temperature in a container. A lid is laid across the top of the container to slow evaporation. The lid does not prevent ambient air from slowly entering the container. After six months the liquid is yellowish orange.

Example 15

Stability Testing of Serum A

Procedure. The liquid of Example 2, Serum A is stored at 50 degrees Celsius in a container. A lid is laid across the top of the container. After four weeks the liquid is still clear and colorless.

Example 16

Stability Testing of Serum B

Procedure. The liquid of Example 2, Serum B is stored at 50 degrees Celsius in a container. A lid is laid across the top of the container. After four weeks the liquid is brownish orange.

Conclusion of Stability Testing. Composition of Serum A (Ascorbyl gluconate) is more stable than Serum B (Ascorbic acid).

Clinical Testing for the Treatment of Skin Condition.

Clinical Testing I: Serum A versus Placebo.

Ballistometry showed a decrease in skin stiffness at 1 week in the treated group, and an increase in the placebo group. The placebo group continues to increase in stiffness at one month. This study started in the late summer and as the season changes the temperature has dropped considerably and the humidity is lower. Typically we start to see the onset of drier skin as colder weather progresses. The amplitude measurement has a decrease in the placebo group, but the treated group had a slight increase. As skin ages, we generally see a decrease in the amplitude measurement.

Laser Doppler: There was an increase in the microcirculation of the skin at the 1-week measurement in both the placebo and treated groups. There was no change at the 1-month measurement.

Silastic Castings: These results are reported as % change in fine lines and wrinkles. The castings at 1 week and 1 month were compared to the baseline castings. The castings obtained from the treated group showed a greater decrease in fine lines and wrinkles.

| Fine Lines & Wrinkles | | | | |
|---|---|---|---|---|
| | | Increase | No Change | Decrease |
| PLACEBO | 1 Week | 63 | 30 | 7 |
| | 1 Month | 70 | 23 | 7 |
| TREATED | 1 Week | 30 | 30 | 40 |
| | 1 Month | 25 | 25 | 50 |

Photographic Assessment at 1 Month:
Photographs were evaluated for skin texture, pigmentation, pore-size, skin tone and clarity.
Treated- 8 of 15 subjects showed an overall improvement in their skin.
Placebo- 2 of 15 subjects showed an overall improvement in their skin.

Conclusions of Clinical Testing (I).
1. Comparison of the Treated group versus the Placebo group exhibited:
   Reduced breakouts.
   Softer skin, smoother complexion.
   Skin looks and feels brighter and fresh.
   Reduced pore-size, less facial oil.
2. Subject's Assessment of their skin:
   The subjects were asked to evaluate the skin care regimen that they were prescribed.
Placebo—6 of 15 report a positive response to the prescribed skin care.
Treated—14 out of 15 report a positive response to the prescribed skin care
3. Safety/Adverse Reactions:

There were no reported incidences of skin irritation during this study.

Clinical Testing II: Serum A Versus Serum B Versus Placebo.

The study was a double blinded, pilot, controlled, single center study. A total of 24 subjects participated in the study. They were divided into two groups of 12 subjects each. The test samples (with and without ascorbyl gluconate) were made as described in Example 2. Group-A, applied the Serum-A, while the Group-B applied the Serum-B. Each subject was asked to use the given test products on left under-eye for a period of 4 weeks. The right under-eye was the untreated eye. The subjects were assessed on 0 day, and at the end of the $1^{st}$, $2^{nd}$, $3^{rd}$ and the $4^{th}$ week. The assessment was carried out by a Dermatologist for the improvement in the (1) dark circles, (2) puffiness, and (3) wrinkles under the eye. Elastometer readings were taken for the crowfeet area to assess the improvement in skin elasticity.

2.1 Investigational Products.
   The investigational products were the two under eye serum formulations and were coded A and B as follows:
   Serum from Example 2: Serum-A (With ascorbyl gluconate).
   Serum Modified from Example 2: Serum-B (Only ascorbic acid, no ascorbyl gluconate).

2.2 Controls for the Study.
   The right under-eye was untreated and that was taken as the control untreated site.
  2.3 Subject Population.
   Total 24 subjects were selected as per the inclusion and exclusion criteria.
  2.4 Inclusion Criteria:
   i. Male and Female (30:70) subjects in generally good health.
   ii. Subjects in the age group of 25-45 years.
   iii. Subject has not participated in a similar investigation in the past four weeks.
   iv. Subjects have not used similar products for the last 4 weeks.
   v. Subjects willing to give a written informed consent and come for regular.
   vi. Follow-up.
   vii. Subjects should have an under eye puffiness score of 2-3, and under eye dark circle score of 2-3 as mentioned in section 9 of this protocol.
  2.5 Exclusion Criteria
   i. A Known history or present condition of Allergic response to any cosmetic product.
   ii. Subject having skin disease (e.g. psoriasis, atomic dermatitis or other cutaneous manifestations), which would interfere with the test readings.
   iii. Subjects having melasma.
   iv. Subjects on medications (e.g. steroids or antihistamines), which would compromise the study.
   v. The subject is pregnant/nursing.
  2.6 Duration of Study: Four Weeks.
  3.0 Study Outline.
  3.1 Product Application.
   The respective test sample was provided to the subjects after the baseline reading. The subjects applied approximately 0.5 grams of the test products on the left under-eye and evenly spread the product gently extending up to the crowfeet region with light strokes till absorbed into the skin. The right under-eye was considered as control or untreated site. The test sample was applied twice daily (i.e. once after bath and second before bedtime) for a period of four weeks on the left under eye region.
  3.2 Clinical Measurements.
  3.2.1 Visual Assessment of Under-eye (By Dermatologist).
   The dermatologist graded the both the under-eyes of the subjects on the baseline day and at the end of the $1^{st}$, $2^{nd}$, $3^{rd}$ and $4^{th}$ week as per the following criteria.
  (1) Dark circles—The dermatologist graded the under eye dark circles on both the left and right under-eye by using the following scale (half points used when necessary):

| Description | Score |
|---|---|
| No dark circles | 0 |
| Mild dark circles | 1 |
| Moderate dark circles | 2 |
| Severe dark circles | 3 |

(2) Puffiness—The dermatologist graded the under eye puffiness on both the left and right under-eye by using the following scale (half points used when necessary):

| Description | Score |
|---|---|
| No puffiness | 0 |
| Mild puffiness | 1 |
| Moderate puffiness | 2 |
| Severe puffiness | 3 |

(3) Wrinkles—The dermatologist graded the under eye wrinkles on both the left and right under-eye by using the following scale (half points used when necessary):

| Description | Score |
|---|---|
| No wrinkles | 0 |
| Very fine lines | 1 |
| Moderate wrinkles | 2 |
| Deep set wrinkles | 3 |

3.2.3 Instrumental Assessment.
Elastometer: Skin elasticity of both the crowfeet area was recorded using Elastometer.
4.0 Results and Statistical Analysis.
4.1 Dermatologist's Assessment.
4.1.1 Dark circles.
Serum-A. Compared to the baseline scores, there is a good improvement in the dark circle scores for the treated under-eye. The scores for the untreated under-eye also seem to improve albeit only to a small extent.
Serum-B. Compared to the baseline scores, there is a good improvement in the dark circle scores for the treated under-eye. The scores for the untreated under-eye also seem to improve albeit only to a small extent. However, the differences in improvement between untreated & treated under-eye scores are not statistically significant. 5 of the 12 subjects in the Serum-B group showed significant improvement in the reduction of dark circles.
Serum-A Compared to Serum-B. If the improvements in the scores for the treated under-eye over the improvements in the scores for the untreated under-eye are compared, there is no statistically significant difference between the improvement in dark circles due to Serum-A and Serum-B, although the stability of Serum A is better.
4.1.2 Puffiness.
Serum-A. Compared to the baseline scores, there is a good improvement in the puffiness scores for the treated under-eye. The scores for the untreated under-eye also seem to improve albeit only to a small extent.
Serum-B. Compared to the baseline scores, there is a good improvement in the puffiness scores for the treated under-eye. The scores for the untreated under-eye also seem to improve albeit only to a small extent.
Serum-A Compared to Serum-B. If the improvements in the scores for the treated under-eye over the improvements in the scores for the untreated under-eye are compared, there is no statistically significant difference between the improvement in puffiness due to Serum-A and Serum-B, although the stability of Serum A is better.
4.1.3 Wrinkles.
Serum-A. Compared to the baseline scores, there is a good improvement in the scores for wrinkles for the treated under-eye. The scores for the untreated under-eye also seem to improve albeit only to a small extent.
Serum-B. Compared to the baseline scores, there is a good improvement in the scores for wrinkles for the treated under-eye. The scores for the untreated under-eye also seem to improve albeit only to a small extent.
Serum-A Compared to Serum-B. If the improvements in the scores for the treated under-eye over the improvements in the scores for the untreated under-eye are compared, Serum-A shows better improvement in reduction of wrinkles post week-3, and the stability of Serum A is better.
4.2 Instrumental Assessment of Crowfeet Area: Elastometer.
Serum-A. Compared to the baseline scores, there is an improvement in the Elastometer readings scores for the treated crowfeet area. Eight of the 11 subjects show significant improvement in Elastometer readings for the treated crowfeet area.
Serum-B. Compared to the baseline scores, there is an improvement in the Elastometer readings scores for the treated crowfeet area. However, the extent of improvement is fluctuating over the four-week period.
Serum-A Compared to Serum-B. There is no statistically significant difference between Serum-A and Serum-B, although serum A is directionally better, and the stability of Serum A is also better.
CONCLUSION OF CLINICAL TESTING.
Based on the data it is generally seen that for all the under-eye attributes (dark circle, puffiness, and wrinkles), good amount of improvement is seen after week-3 for Serum-A (Ascorbyl gluconate), compared to untreated area.

The invention claimed is:
1. Ascorbyl ester of formula (I), its isomers, and salts thereof;

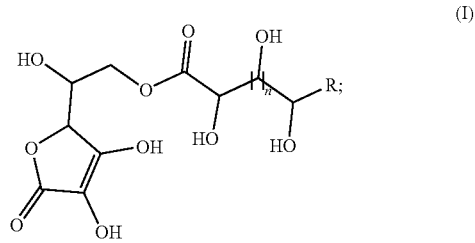

Wherein,
n=0, 1, 2, and 3; and
R=H, —CH$_2$OH, —CH(OH)—CH$_2$OH, and —CH(OH)—CH(OH)—CH$_2$OH.
2. A composition comprising the ascorbyl ester of claim 1 for the treatment of acne, collagen loss, loss of skin pliability, loss of skin suppleness, skin wrinkles, fine lines, and dark circles under the eyes.
3. A composition comprising the ascorbyl ester of claim 1, wherein said ascorbyl ester is Ascorbyl gluconate, the chemical name of which is 2-(3,4-Dihydroxy-5-oxo-2,5-dihydro-furan-2-yl)-2-hydroxyethyl 2,3,4,5,6-pentahydroxyhexanoate.
4. A composition comprising the ascorbyl ester of claim 1, wherein said ascorbyl ester is Gluconyl Ascorbate, the chemical name of which is (3,4,5-Trihydroxy-6-oxotetrahydro-2H-pyran-2-yl) methyl (2Z)-2,3,4,5,6-pentahydroxyhex-2-enoate.

5. A composition comprising the ascorbyl ester of claim 1, and a carrier or base.

6. A composition comprising the ascorbyl ester of claim 1 for topical application.

7. A method for preparing the ascorbyl ester of claim 1, said method comprising (1) combining (i) a polyhydroxy lactone, (ii) ascorbic acid, and (iii) a liquid reaction medium to form a composition, and (2) heating said composition from 50 to 120 degrees Celsius at a pH of 3.0 to 5.5.

8. A process according to claim 7, wherein said liquid reaction medium is selected from the group consisting of water, ethanol, ethylene glycol, propylene glycol, butylene glycol, pentylene glycol, hexylene glycol, polyethylene glycol, polypropylene glycol, glycerin, Diglycerin, polyglycerol, sorbitol, polysorbate, methylpropanediol, ethoxydiglycol, dimethyl sulfoxide, N-methyl pyrrolidone, pyrrolidone, and combinations thereof.

9. A process according to claim 8, wherein said liquid reaction medium is polyethylene glycol.

* * * * *